United States Patent [19]
Kramer, III

[11] Patent Number: 5,954,676
[45] Date of Patent: Sep. 21, 1999

[54] VERSATILE SPLINTING DEVICE

[76] Inventor: Warren G. Kramer, III, 324 Emerald Bay, Laguna Beach, Calif. 92651

[21] Appl. No.: 08/961,060

[22] Filed: Oct. 30, 1997

Related U.S. Application Data

[63] Continuation of application No. 08/486,985, Jun. 7, 1995, abandoned.

[51] Int. Cl.[6] ........................................................ A61F 5/04
[52] U.S. Cl. ..................................... 602/6; 602/8; 602/13; 602/20; 602/23; 128/DIG. 20
[58] Field of Search ................................ 602/5–9, 13, 20, 602/23; 128/DIG. 20

[56] References Cited

U.S. PATENT DOCUMENTS

| | | | |
|---|---|---|---|
| 3,674,021 | 7/1972 | Snyder et al. | 602/8 |
| 4,178,923 | 12/1979 | Curlee | 602/13 |
| 4,182,320 | 1/1980 | Sweeney | 602/13 |
| 4,483,332 | 11/1984 | Rind | 602/13 |
| 4,537,184 | 8/1985 | Williams, Jr. | 602/8 |
| 4,793,330 | 12/1988 | Honeycutt et al. | 602/8 |
| 4,852,557 | 8/1989 | Grim | 602/8 |
| 5,286,249 | 2/1994 | Thibodaux | 602/12 |
| 5,311,882 | 5/1994 | Gagne | 128/DIG. 20 |
| 5,318,504 | 6/1994 | Edenbaum et al. | 602/8 |
| 5,372,575 | 12/1994 | Sebastian | 602/13 X |
| 5,437,614 | 8/1995 | Grim | 602/19 |
| 5,520,621 | 5/1996 | Edenbaum et al. | 602/8 |

FOREIGN PATENT DOCUMENTS

| | | | |
|---|---|---|---|
| 4423755 | 1/1995 | Germany | 602/6 |

*Primary Examiner*—Richard J. Apley
*Assistant Examiner*—Victor K. Hwang
*Attorney, Agent, or Firm*—Lyon & Lyon LLP

[57] ABSTRACT

A field splinting device that can also be used instead of a fiberglass or cardboard cast for injured limbs, particularly severe sprains and fractures is proposed. The device is waterproof and is radiotranslucent. The device utilizes two sets of multi-layer formable materials, such as fiberglass shims located in pouches in first and second members having re-sealable bladders or sheaths to provide structural support on each side of the limb. Pressurizable-bladders are located to the inside of the formable materials to provide cushioning for the limb, and may be inflated by attaching a small inflation bulb to an inlet/outlet port located at each end of the bladder. Each bladder can be independently inflated or deflated to a desired inflation level. A further embodiment is shown having a single sheet of formable material and a single bladder.

6 Claims, 6 Drawing Sheets

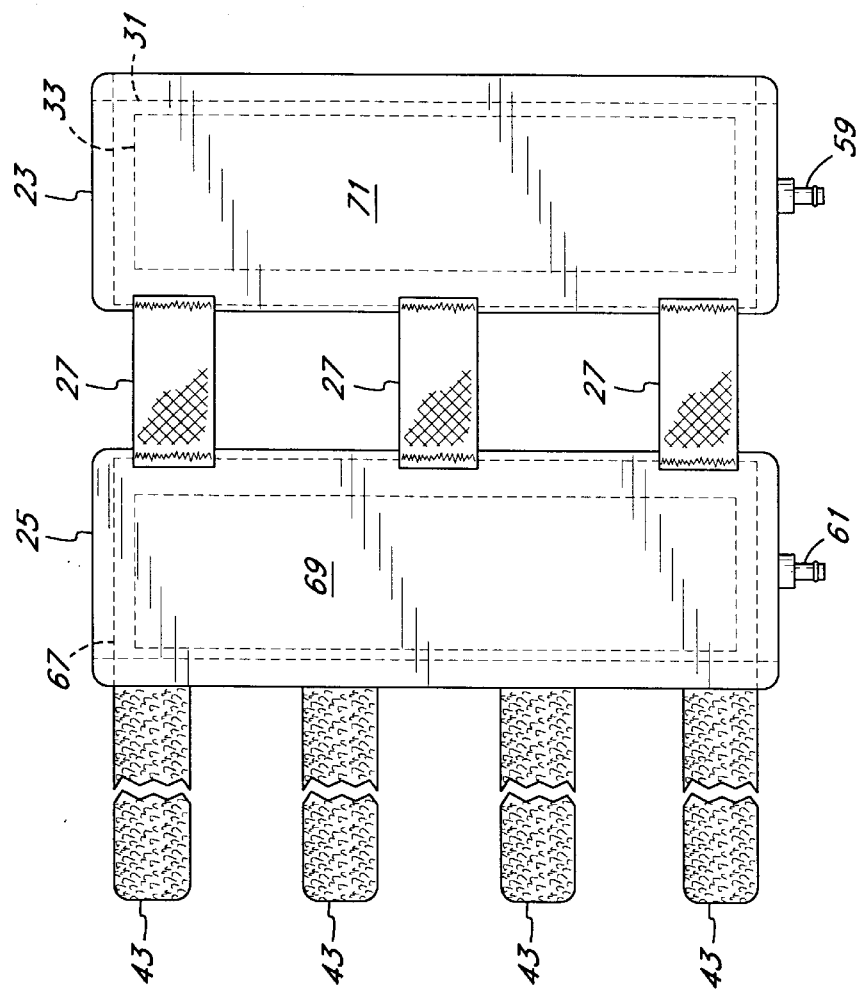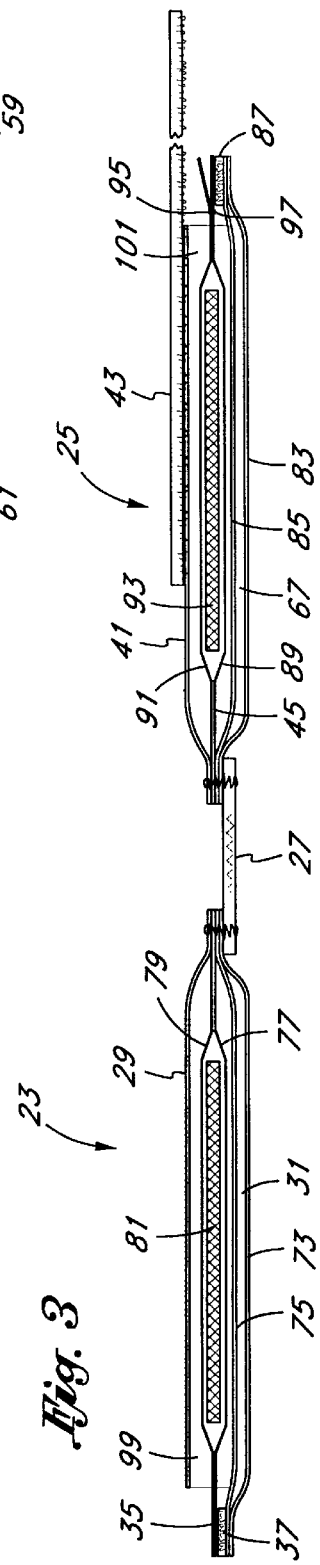

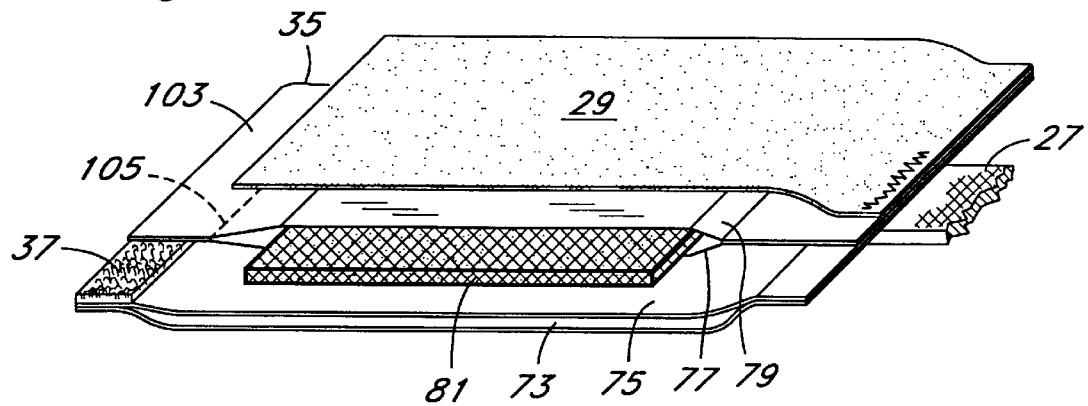
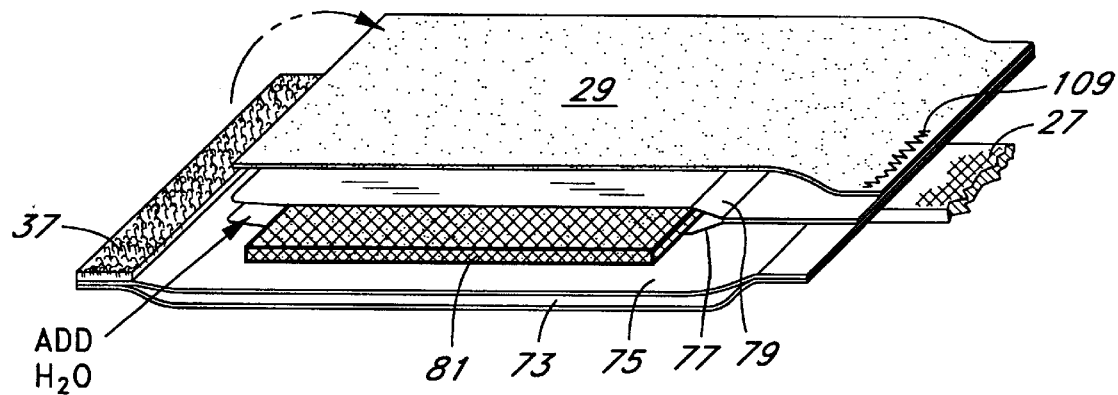
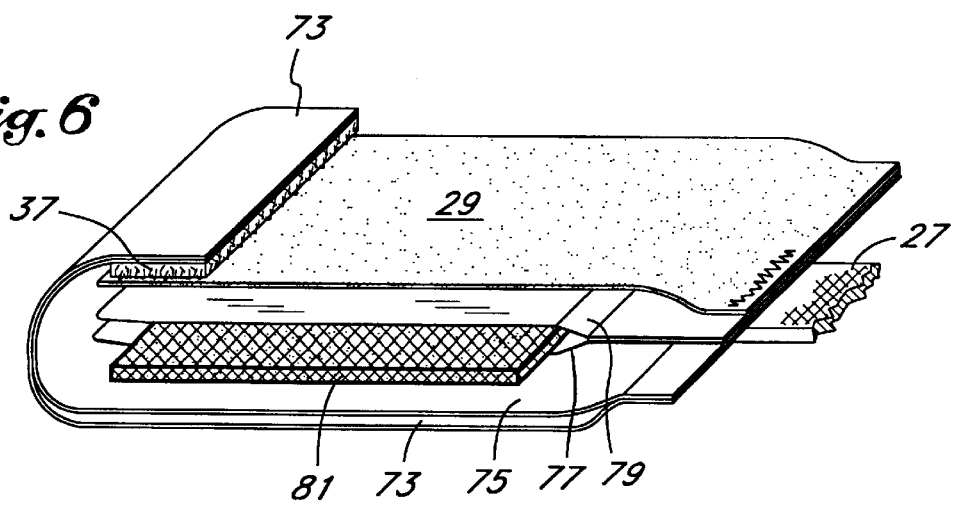

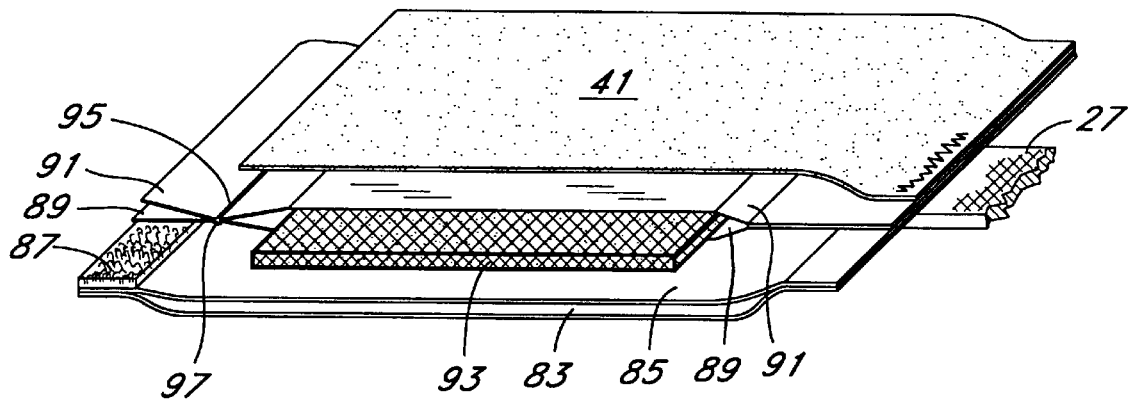
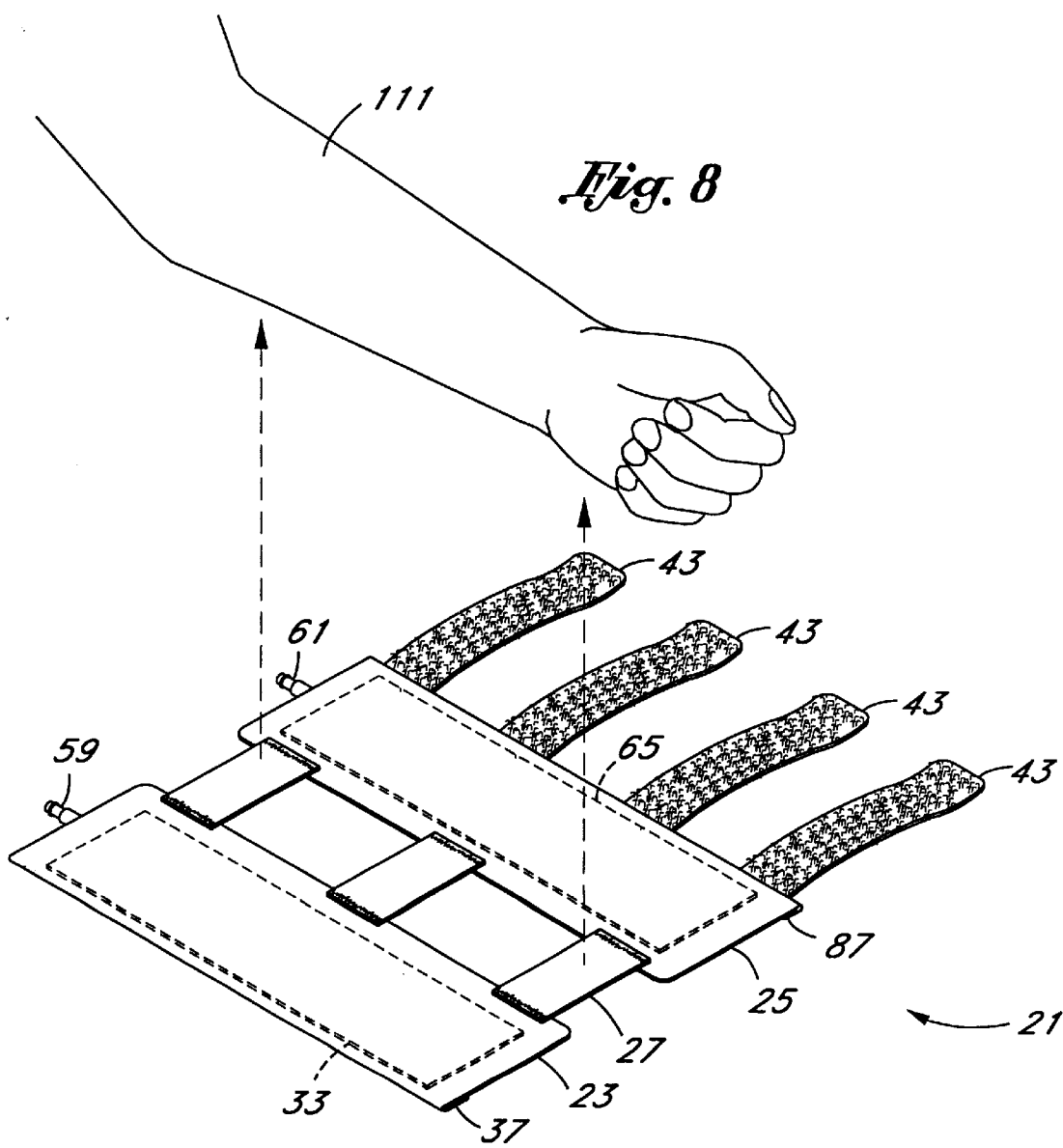

VERSATILE SPLINTING DEVICE

This is a continuation of application Ser. No. 08/486,985 which parent application was filed on Jun. 07, 1995, now abandoned.

FIELD OF THE INVENTION

The present invention relates to the field of medical devices and emergency field medical devices. More specifically, the present invention relates to a versatile splint system for rapid and efficient immobilization of an injured extremity which will facilitate protection, healing, examination, and enable varying levels of pressure to be exerted on the immobilized extremity.

BACKGROUND OF THE INVENTION

Field splinting devices used to support injured limbs or immobilization have been constructed of vinyl, cardboard, foam, air-socks, and nickel-aluminum. Placed against the injured limb, these devices form a support structure to protect the limb during transport to a medical facility. If deemed appropriate by the attending physician, the temporary splint is removed and replaced by a fiberglass cast which is formed in a custom, rigid manner around the injured limb in a clinical setting, usually a physician's office.

Orthopedic casts now commonly used in the treatment of bone breaks and fractures and general limb immobilization are made from fiberglass impregnated with a substance that hardens into a rigid structure. This substance is harder, is waterproof, and more durable than plaster of paris casts, and is radiotranslucent. U.S. Pat. No. 4,411,262 (von Bonin) and U.S. Pat. No. 4,502,479.

Other orthopedic bandages containing other materials generally do not provide the structural strength afforded by fiberglass as dictated by the requirement of having the patient ambulate. However, these bandages do provide some degree of padding for the comfort of the patient.

There are inherent drawbacks to currently available splinting devices and fiberglass casts. Field splinting devices such as cardboard or foam provide only one aspect of limb protection, are not designed to provide a custom fit to the limb, have dimensional limitations, occasionally require additional materials (tape, bandages), and are not considered appropriate devices for after-care protection. Most importantly, they can be difficult to place on the limb due to their rigid structure or application method. This can be of concern as many limb traumas are not easily accessed, and need to be splinted in an angular position.

Although used as the standard of care in post-treatment applications, significant limitations inhibit the fiberglass casting material for use in field applications. Firstly, the entire cast material must be soaked in water and then wrapped circumferentially around the limb, with risk of blood flow restrictions with post-injury swelling. This is often impossible in field situations. Secondly, the splint must be removed and discarded upon arrival to an emergency department or office if a clinician wishes to examine the limb. Thirdly, once in place, the patient can not remove for washing the injured limb. Lastly, once destroyed, a new cast must be formed.

SUMMARY OF THE INVENTION

The specifics of the invention are the provisions for the integration of four major materials and their application: the use of flexible webbing to centrally cradle the injured limb thereby providing stability and the foundation for the integrated device; the use, design, and packaging of self-curing fiberglass shims located in separate bladders or sheaths to provide custom support and rigid protection of the injured limb; the use of adjustable, separate air bladders to provide adjustable, custom support, secure the position of the limb, and encase the injured limb, including minimizing trauma to the skin caused by rigid devices by virtue of its soft air cushioned inner liner (OR Skin Material Interface); and the use of self-adhering adjustment straps to wrap the limb and secure the device. The entire device can be customized for each application at the field site. The device is waterproof, radiotranslucent, is compact and lightweight for storage and transport, and accommodates the mobility of the injured limb. This device allows for increased flexibility in the application of a field splinting device. The device accommodates both the length and circumference of the injured limb because of its flexible design; the limb can be splinted in the position it is found because the device is not rigid until the clinician activates the fiberglass. The fiberglass shims can be used in conjunction with or independently of the air bladders. Independently, each provide support and protection of the injured limb equal to devices of the same purpose. In combination, they provide superior support and protection not afforded by independent devices. The fiberglass shims can be custom molded to the length, circumference, shape, and position of the limb. The air bladders can be adjusted to accommodate for swelling and changes in position. The straps can be adjusted for the amount of air in the air bladders and for the position of the limb.

Other objects, features, and design advantages of the present invention will be in part apparent and in part pointed out hereinafter.

BRIEF DESCRIPTION OF THE DRAWINGS

The invention, its configuration, construction, and operation will be best further described in the following detailed description, taken in conjunction with the accompanying drawings in which:

FIG. 2 is a plan view of a first embodiment as shown in FIG. 1 but illustrating the interior portion of the first and second members which are directed toward the extremity to be immobilized;

FIG. 3 is a cross sectional view of the embodiments of FIGS. 1 and 2 and illustrating the layers of material inside the splint;

FIG. 4 illustrates in an open layered view the relationship of the layers of the splint of the present invention as they exist immediately before opening the enclosure securing the formable material to begin the curing process;

FIG. 5 illustrates in the open layered view as was shown In FIG. 4, the relationship of the enclosure securing the formable material after the enclosure has been opened;

FIG. 6 illustrate sin the open layered view as was shown In FIGS. 4 and 5, the relationship of the exterior portions of the splint as they are brought to secure the enclosure and the formable material after curing has been initiated;

FIG. 7 illustrates in the open layered view similar to that shown In FIGS. 4–6, but illustrating a re-sealable enclosure which was shown in FIG. 3;

FIG. 8 illustrates the position of the splint of the present invention in position to accept a human arm, as a member to be immobilized, into the splint so that it may be secured;

DETAILED DESCRIPTION OF THE PREFERRED EMBODIMENT

Figure 1:
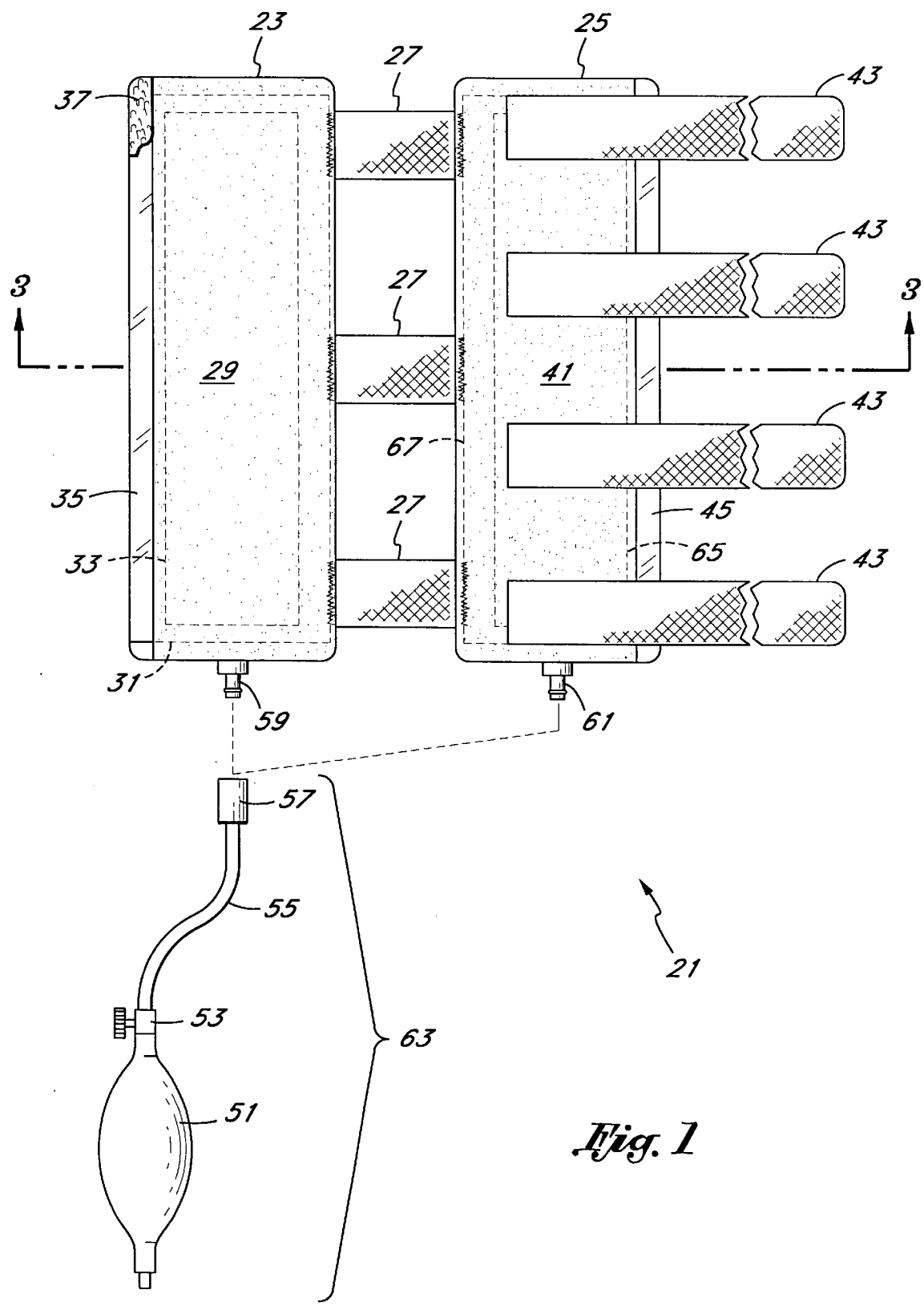
FIG. 1 is a plan view of a first embodiment of the splint of the present invention and illustrating the exterior portion of the first and second members which are directed away from an extremity to be immobilized, joined by a web, fastening members and a source of fluid pressure connected to the first and second members.

The description and operation of the invention will be best described with reference to FIG. 1. FIG. 1 is a plan view of a first embodiment of a splint 21 and showing the surfaces which will generally face away from the member to be immobilized. The splint 21 has a first member 23 and a second member 25 connected by three flexible members 27. The flexible members 27 may be sewn webbing, polymeric material, or even formed integrally with any of the layers of material which will later be described.

The first member 23 has a generally open outer surface 29, which will be made of a material which can act as the loop material of a hook and loop fastener set. This surface will be used in conjunction with hook fasteners not only to secure the splint as a whole, but also to secure an inner pocket of the first member 23.

Two areas are shown in dashed line format on first member 23 and meant to demark the boundaries of internal structure. The bladder 31 may be made of flexible material, as for example, vinyl, polyvinylchloride, polyethylene, nylon, polyester, or any combination thereof.

The inner most dashed line indicates a first sheet or expanse of formable material 33. To the left of the boundary of the outer surface 29, an exposed layer of a first enclosure 35 is seen. The uppermost portion of the first enclosure 35 is shown in a partially broken away format to show an abbreviated portion of a first flap of hook members 37 which may extend the length of the first member 23, and are oriented to engage with the portion of outer surface 29 lying immediately adjacent the portion of the first enclosure which is exposed in FIG. 1.

The second member 25 has an outer surface 41 which supports a series of flexible hook fasteners 43, of which four such fasteners 43 are shown in conjunction with the splint 21. The splint 21 may have a greater or lesser number of the fasteners 43 especially inasmuch as the size of the splint 21 may vary from a large size to immobilize a human leg or a smaller size for a forearm, which will be shown for illustrative purposes in the instant patent application. The flexible hook fasteners 43 are shown in FIG. 1 with the hooks facing away from the observer, so that they may extend completely around and engage onto the surface 29.

In a mirror fashion with respect to that of first member 23, the second member 25 has an exposed layer of a second enclosure 45. It is understood that the enclosures 35 and 45 need not be so dimensioned that they extend from the first and second members 23 and 25, and can be such that the user would have to reach into the first and second members 23 and 25 in order to manually access the enclosures 35 and 45.

The points of attachment on the surface 41 of the flexible hook fasteners 43 leave a strip of space along the surface 41 adjacent the enclosures 35 and 45 to enable a second flap of hook members which are not visible in FIG. 1, to engage the surface 41.

Below the lower ends of the first and second members 23 and 25 a squeeze bulb 51 is shown having a pressure release valve 53, and fluid supply hose 55. At the end of the fluid supply hose 55, a fitting 57 is shown which is compatible with both a first quick release fitting 59 on the first member 23 and a second quick release fitting 61 on the second member 25. The quick release fitting 59 allows the inlet to the bladder 31 to be selectively sealed, by pushing the fitting 57 inwardly toward the air bladder 31, or unsealed by pulling the fitting 57 outwardly from the air bladder 31. One embodiment of the fitting 59 is a push-pull valve, and is commercially available designated as model no. 320-AC, and is sold by Halkey-Roberts, Inc. of St. Petersburg, Fla.

It is preferable that such fitting be used since the fittings 59 and 61 act as a check valve to prevent the flow of fluid into the first and second members 23 and 25 when the fitting 57 is detached from the fittings 59 and 61. However, when the fitting 57 is attached to the fittings 59 and 61, fluid can flow toward the squeeze bulb 51 and be bled off by the release valve 53.

The cast 21 includes inflatable bladders to increase or decrease the pressure against the extremity to be immobilized. In this configuration, the first and or second members 23 and 25 can be inflated, then disconnected from fitting 57 to then hold their pressure. Thus eliminated is the need to keep an inflation device 63, made up of squeeze bulb 51, pressure release valve 53, fluid supply hose 55, and fitting 57. It is also clear in this configuration, and with the quick release and sealing fittings 59 and 61 that the fluid supply hose 55 may be eliminated, with the fitting 57 connected directly adjacent the pressure release valve 53.

The structures within the second member 25 also mirror the structures within first member 23 and which are also shown in dashed line format. The second member 25 has a second sheet or expanse of formable material 65, and a second bladder 67. The first bladder 31 of the first member 23 is in fluid contact with the fitting 59. The second bladder 67 of the second member 25 is in fluid contact with the fitting 61.

Referring to FIG. 2, a plan view of the opposite side of the splint 21 is shown in which the hook members of the series of flexible hook fasteners 43 are exposed to the observer. The first member 23 is shown as having an inner surface 71 while the second member 25 is shown as having an inner surface 69. These inner surfaces 69 and 71 may be an actual part of the bladders 67 and 31. In the alternative, the bladders 67 and 31 may be placed within material similar to the soft outer surfaces 29 and 41, or the portions of the bladders 67 and 31 exposed may be coated with a heat insulative material or linty material to enhance comfort to the wearer.

Further, the length of the three flexible members 27 may be varied to give more open space or more closed space between the first and second members 23 and 25. In the alternative, the flexible members 27 may be replaced by a single flexible member which extends approximately the length of the first and second members 23 and 25 to eliminate any open areas.

Referring to FIG. 3, a cross sectional view taken along line 3—3 of FIG. 1 reveals the layers within the splint 21. The bladder 31 is shown as being formed by a sheet of material 73 (which has side 71) joined to a sheet of material 75 at their respective common outer edges. In FIG. 3, their joinder as shown in cross section is just below the first flap of hook members 37, and at the edge where the first member 23 is attached to the flexible member 27. Thus the bladder 31 includes the sheets of material 73 and 75 as well as the space in between.

Also shown joined to the flexible member 27 is the end of a first enclosure 35. The first enclosure 35 is made up of a first layer 77 and a second layer 79, and encloses a first sheet of formable material 81. The first sheet of formable material 81 can include a fiberglass/resin material which cures on exposure to air, or a traditional plaster material which requires the introduction of water to begin the curing process. Such material which will usually but not always be in planar form will be available completely sealed within the first enclosure 35. The first enclosure 35 may be made of foil. The first sheet formable material 81 may be a resin matrix commercially available from Carapace, Inc. of Tulsa, Okla. 74147, and is sold commercially under the name ENDURASPLINT2™. This material, which, when exposed to moisture via the air in the atmosphere or water from an external source, cures over time to a rigid state. During the curing process of the first sheet of formable material 81, the user can allow for the molding of the splint 21 around the extremity to be immobilized.

To begin the curing process of the first sheet of formable material 81, the material must be exposed to moisture by opening the first enclosure 35. One manner of opening the first enclosure 35 would be a tear cut, such that the portion of the first enclosure 35 adjacent the first flap of hook members 37 can be completely removed.

In this case, where water is added to begin the cure, some of the moisture may leak from within the first enclosure 35 and may cause the outer surface 29 to become wet. The leakage is typically not a problem from an operational standpoint, and does not affect the performance of the device. A re-sealing closure can be used instead of the tear away strip made by scoring the joined surfaces of the enclosure 35.

On the right side of the splint 21 of FIG. 3, bladder 67 is shown as being formed by a sheet of material 83 (which has side 69) joined to a sheet of material 85 at their respective common outer edges. In FIG. 3, their joinder as shown in cross section is just below a second flap of hook members 87, and at the edge where the second member 25 is attached to the flexible member 27. Thus the bladder 67 includes the sheets of material 83 and 85 as well as the space in between.

Also shown joined to the flexible member 27 is the end of a second enclosure 45. The second enclosure 45 is made up of a first layer 89 and a second layer 91, and encloses a second layer of formable material 93. The second layer of formable material 93 will typically be identical with that of the first layer of formable material 81, although the splint 21 can accommodate differences not only with respect to formable material 93, 81, but also with respect to the relative sizes, including lengths and widths of the first and second members 23 and 25.

As another manner for allowing access to one of the first and second enclosures 35 and 45, second enclosure 45 is shown as having re-sealable ribs, such as may be commonly commercially available in conjunction with freezer bags. First layer 89 carries a lower sealing rib 97, while the second layer 91 carries an upper sealing rib 95. The sealing ribs 95 and 97 interlock to form an openable and re-sealable second enclosure 45. FIG. 3 illustrates the sealing ribs 95 and 97 in sealed position. With the sealing ribs 95 and 97, the ends of the first and second layers 89 and 91 may lie loosely open to facilitate manual opening of the second enclosure 45. Both the first and second enclosures 35 and 45 may be fitted with sealing ribs such as sealing ribs 95 and 97. Both methods of opening the enclosures 35 and 45 are shown for completeness.

As can be seen from FIG. 3, once the tear away portion joining the layers 77 and 79 has been removed, the first flap of hook members 37 may be brought over and onto the outer surface 29 to envelope the first sheet of formable material 81, and what may remain of the enclosure 35, within a pouch 99. The pouch 99 is formed by the inside surface of the loop type material which formed the outer surface 29, and the sheet of material 75 which formed one side of the bladder 31. Similarly, second 25 has a pouch 101 which is formed by the inside surface of the loop type material which formed the outer surface 41, and the sheet of material 85 which formed one side of the bladder 67.

Referring to FIG. 4, a showing of how the tear away strip on the enclosure 35 would operate is illustrated by the use of a sectional view including staggered layers. The first enclosure 35 has a tear away portion or strip 103, which has an expected margin of separation shown as dashed line 105. In reality, and depending upon the materials used, the separation line 105 can be produced by scoring, or simply allowed to tear, as in the case of some plastic materials which tear easily once a tear or shear area has been provided.

FIG. 4 is a sectional view, and does not show the first enclosure 35 at a point upstream, where the tear may be facilitated by a v-shaped notch or simple cut in the side of the first enclosure at its end (not shown). Other alternatives for opening sealed packaging are known, and include pull strings, and can even include a tape sealer which can be rapidly removed. Given that the present invention is advantageous for use in first aid service, the manner provided for the first enclosure 35 to be unsealed should be considered for quickness in opening. Even if the first enclosure 35 does not tear evenly, to leave a pair of even edges or widths of first layer 77 and a second layer 79, the invention will still work well.

FIG. 5 illustrates the first portion 23 of the splint 21 after the strip 103 has been removed. Typically, the first portion 23 will be opened in a position where the first portion 23 will be held vertically with the tear away strip 103 being removed from the uppermost edge of the first portion. Then, the areas around the formable material 81 will be available for the introduction of water, when water is used as a curing initiator. Where water is used, the splint 21 can be crushed together and squeezed together to insure rapid distribution of the water. Note that the exposure of the formable material 81 will enable the addition of water to both sides of surfaces of the formable material 81.

In the present embodiment, the formable material 81 is shown lying between the first layer 77 and second layer 79. It is possible to adhere the formable material 81 to one of the first and second layers 77 and 79, either by an adhesive or other means. In the alternative, and where it can be done without exposing it to the environment, the formable material 81 can be sewn or otherwise mechanically connected to one of the first and second layers 77 and 79. Still another way of anchoring the formable material 81 would be for it to be extended into a sewn area 109 where the layers 75, 73, 77, 79, and 29 and flexible members 27 are joined.

This is not to say that the splint 21 need have any sewn areas. Any of the areas of the materials making up the splint 21 can be joined by welding, bonding, or the like. The manner of joining will largely depend upon the selection of materials. For example, the flexible members 27 could be made of the same material as, and coextensive with the layers 73 and 75, and the layers 83 and 85. In effect, the bladders 31 and 67 could be made together, with the portions of the layers 73 and 75, and the layers 83 and 85 which form the flexible members 27 could be fused or glued together in the same manner in which the peripheral meeting edges of the bladders 31 and 67 are joined. Other manners of configuring the internal layers and interconnectivity of the splint 21 can be equivalently employed and are contemplated by the methods and structures disclosed.

Although FIG. 5 illustrates the addition of water ($H_2O$), the curing process will depend upon the material chosen for the formable material 81. Other methods for initiation of curing may be the mixing of chemicals, or the simple exposure of the formable material 81 to air. All such methods of curing, the initiation of curing, and materials to be cured are contemplated for use with the splint 21 of the present invention.

The function of the formable material 81 can be served regardless of the above mentioned techniques, or techniques to be discovered in the future, for providing the formable material 81. The formable material 81 serves several purposes. First, by hardening, the extremity to be immobilized will be protected against bumping or touching other objects. Where the injury is severe, the patient will be saved further pain trauma, and perhaps further damage to already damaged tissues.

Secondly, the ability to achieve a hard protective shell in conformance with the patient's extremity can only be achieved by providing a material which is hardenable after it has been engaged about the patient's extremity. A preformed protective shell could not provide the more efficient and specific protection to the extent and closeness to which a formable material 81 could provide.

Thirdly, the use of the adjustable and formable cast 21 enables emergency medical technicians to carry one or two sizes of the splint 21 and yet have the ability to service almost any emergency. Perhaps one size for the leg and one for the arm may be all of the stocking variation needed. A pre-formed rigid cast would have to come in a variety of sizes which would mandate a significant stocking space and investment. The lost investment would be insignificant when compared to the lost space in the emergency vehicle where other life-saving materials vie for occupancy.

Fourthly, note referring again to FIGS. 1 and 2 the planar configuration of the cast 21 in its ready-to-use state. It can be supplied as a large flat sheet, or folded in half, or folded in thirds into a small roll. The squeeze bulb 51 and its associated pressure release valve 53, fluid supply hose 55, and fitting 57 may be included with the kit, or used with other squeeze bulbs, such as used for blood pressure measurement. In this case, the elimination of the necessity to carry a bulb with each splint would be eliminated. Where complete self contained operation is needed, a disposable bulb could be provided. One example of such a disposable bulb would be an accordion shaped, palm sized box which could be depressed to fill the bladders 31 and 67 slowly. The small size of these plastic and resilient devices would permit their inclusion into the splint and possibly enable the splint to come with two bulbs already attached to the bladders 31 and 67.

Fifthly, when a break occurs, the necessity for performing an X-ray is manifest. Where a field splint is used which has soft bendable metal, the X-rays cannot be taken unless the field splint is removed due to the fact that the metal portions would obscure the X-ray. In this case, the patient goes from field splint, to temporary splint, to a permanent splint after the X-ray has indicated the type of re-setting or other procedure which needs to be performed. The continual casting and re-casting is expensive, time consuming for the medical attendant, and can be further injurious to the patient.

The use of the splint 21 of the present invention, and which is radiotranslucent, enables adjustments to be made, and X-rays to be taken, without ever having to remove the splint 21. Further, the patient suffers less from having to be re-cast, and the possibility of further injury from the re-casting operation is eliminated.

Lastly, the air bladders 31 and 67 when inflated will allow a comfortable standoff between the extremity to be protected and the relatively rigid formable material 81.

Referring to FIG. 6, the first member 23 is shown with the first flap of hook members folded over and engaged with the outer surface 29 to envelope the first sheet of deformable material 81 and the first layer 77 and second layer 79 of the first enclosure 35. The enveloping action shown is not meant to seal against water leakage, but merely to capture the first sheet of deformable material 81 within the first enclosure 35.

Referring to FIG. 7, the re-sealable version of the enclosure, namely enclosure 45 illustrates the first layer 89 and second layer 91 of the enclosure 45 as being joined by the upper and lower sealing ribs 95 and 97. The layers 89 and 91 extend beyond the sealing ribs 95 and 97 to provide a method for grasping those members to pry the re-sealable apart. The manner of re-sealing is the same as would be used for a typical freezer bag.

Referring to FIG. 8, one of the preferred manners of use is illustrated. An extremity to be immobilized, in this instance a forearm 111 is brought over the splint 21. At this stage of use, both of the first and second sheet of formable material 81 and 93 have had their curing process initiated.

Figure 9:
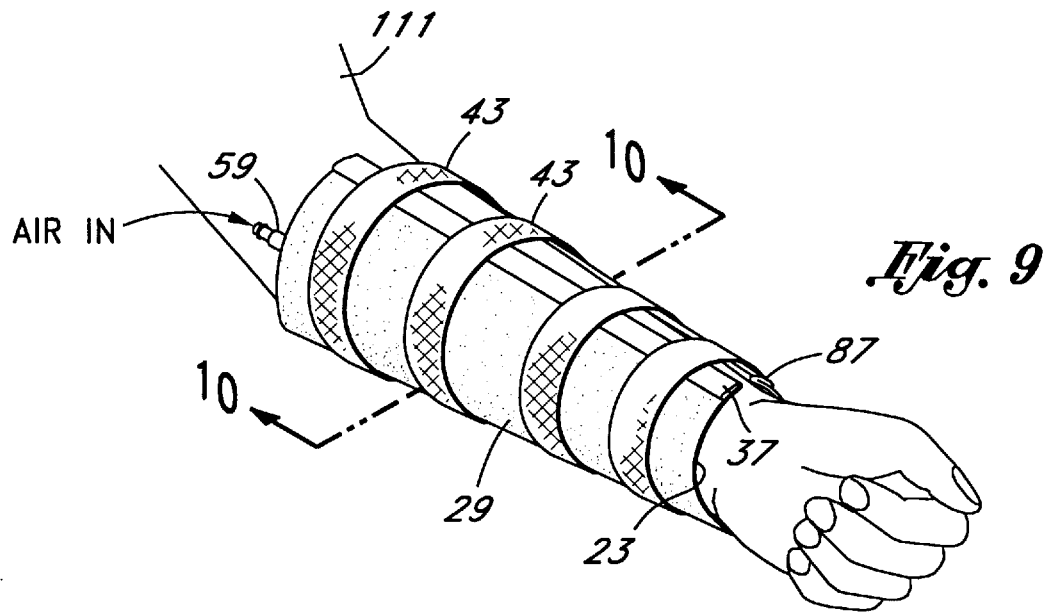
FIG. 9 illustrates the splint of the present invention engaging the arm with fasteners secured and showing the location of one of the air inlets.

The splint 21 is then opened, as shown in FIG. 8, and the splint brought into gentle contact with the forearm 111. As shown in FIG. 9, the series of flexible hook fasteners are brought from the second section 25 and across the top of the first section 23 to engage the surface 29. Note how the splint 21 conforms to the forearm 111. Note the first quick release valve fitting 59 and how it lies unobtrusively along the rearmost portion of the forearm 111.

Figure 10:
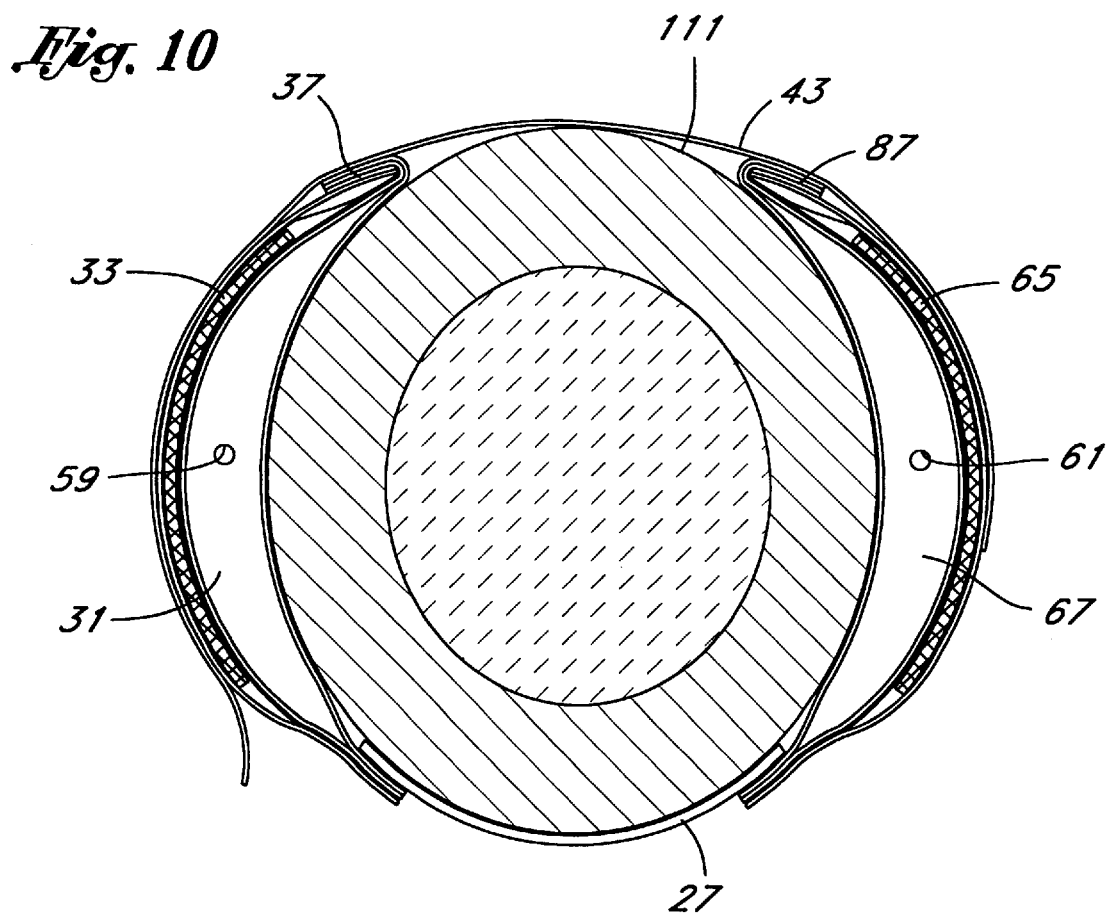
FIG. 10 is a cross sectional view taken along sectional view 10—10 of FIG. 9, and which illustrates the relationship of the internal surfaces of the splint after curing and with the bladders in partially inflated condition.

Referring to FIG. 10, a sectional view taken along line 10—10 of FIG. 9 shows the relationship between the series of flexible hook fasteners 43, and the first and second flap of hook members 37 and 87. The fittings 59 and 61 are visible, as are the bladders 31 and 67. Note how the bladders apply even pressure to the forearm 111 and secure the forearm. Note how the three flexible members 27 encircle the bottom of the forearm 111. As can be seen in FIG. 10, a shortening of the flexible members 27 and widening of the first and second members 23 and 25 would enable the lower portion of the forearm 111 to be protected. Conversely, a lengthening of the flexible members 27 enable more of the tissue of the forearm 111, or other extremity to be isolated, to contact the ambient air.

Figure 11:
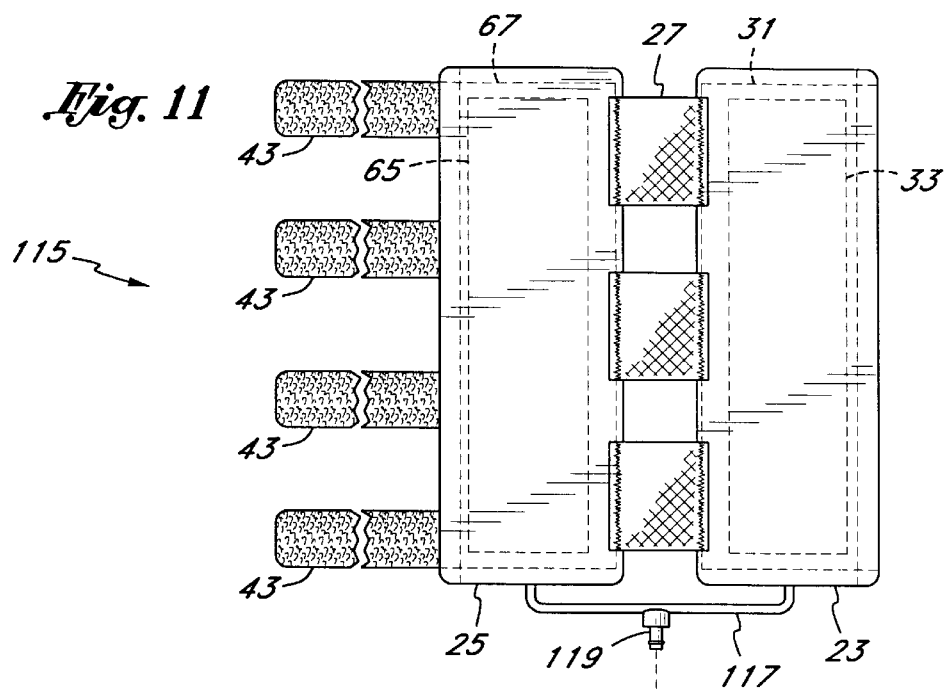
FIG. 11 illustrates a reduced plan view of a further embodiment of the splint of the present invention wherein the flexible webbing has abbreviated lengths and wherein the first and second members have an expanded width, and wherein the bladders are linked by a common fluid passageway length of tubing and having a single fitting.

Referring to FIG. 11, a second version of the splint of the present invention, namely splint 115 is shown in smaller view, but with the three flexible members 27 in a somewhat shorter configuration. In addition, a fluid conduit 117 connects the first bladder 31 with the second bladder 67. This eliminates the need to separately inflate the bladders 31 and 67. In addition, the conduit 117 need not be located at the end of the first and second members 23 and 25, but may be connected between any two of the three flexible members 27.

More importantly, and where the bladders 67 and 31 are formed together, the fluid communication may occur between the bladders 67 and 31 through one or more conduits 117 formed by the layers 73, 75, 83 and 85. The layers 73, 75 83 and 85 may be formed simultaneously to enable such communication. Further, a single fitting 119 is shown. A single fitting, where the bladders 67 and 31 communicate, may be supported by any portion of any of the bladders 67 and 31, or any conduit 117 extending therebetween. The other structures of FIG. 11 were previously discussed with regard to FIGS. 1–10.

Figure 12:
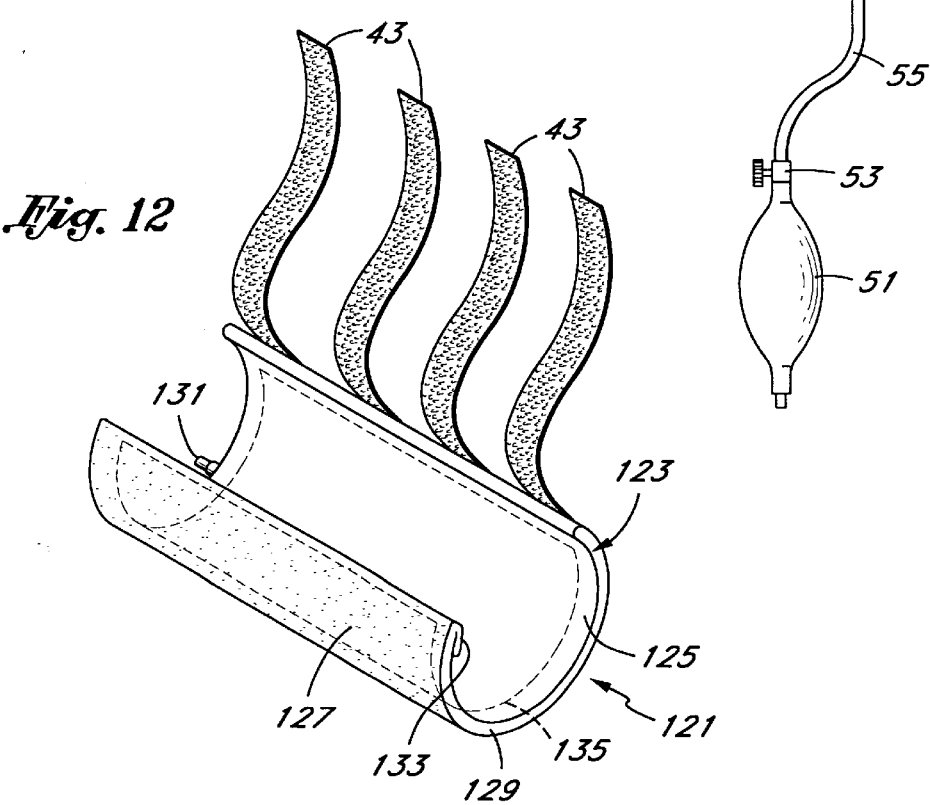
FIG. 12 illustrates a reduced perspective view of a further embodiment of the splint of the present invention having a single member, single pressure fitting.

Referring to FIG. 12, a third embodiment is shown as a splint 121. The splint 121 has a single portion 123 which includes an inner surface 125 and an outer surface 127. The outer surface, much like the surface 29 is preferably made from material which can act as the loop portion of a hook and loop fastener set. Thus, the series of flexible hook fasteners 43 will be able to engage the surface 127. The single portion 123 carries a single bladder 129 which has a fitting 131. The upper edge of the portion 123 which is opposite the row of flexible hook fasteners 43 also has a first flap of hook members 133.

The splint 121 is shown as formed in a semicircular shape to indicate the proper degree of closure for use with an extremity to be isolated, such as forearm 111. Note that the splint 121 is not so wide that it completely encloses the space where the extremity would be located, and is not so narrow as to leave the member to be protected in an unprotected or substantially uncovered position. In this configuration, the filling of the air bladder can control the degree of coverage over the extremity to be immobilized. Partially inflating the bladder 129 before first securing a limb, such as the forearm 111 would cause the splint 121 to cover less of the surface area of the forearm 111.

Also shown in the extent of one or more layers of a single sheet of formable material 135. In general, the sheet of formable material 135 will have a hard surface, but will retain some slight flexibility per unit area. For the single piece embodiment of FIG. 12, it should be simple to urge the upper edges of the split 121 apart to gently remove the extremity to be immobilized, as well as to replace the splint 121 back into place.

In operation, the splints 21, 115, and 121 are versatile splinting devices that can be used to support and protect injured limbs, wrists, and ankles, primarily sprains and fractures. The primary use is to provide custom support for a limb injury outside of a clinical setting. The splints 21, 115, and 121 can also serve as a permanent alternative to traditional plaster or fiberglass casts. This would eliminate the need, expense, and hassle required to remove the field cast or field splint for a more permanent alternative where the alternative would itself be periodically re-placed during the healing process.

In addition, the splint 21, 115 and 121 of the present invention is made to be waterproof and can be removed to bathe the injured limb or extremity. Also, the clinician can readily examine the limb without destroying the cast device where the splint 21, 115 or 121 are used as the cast device.

All of the above advantages of the present invention provide the care-giver and patient more options and save time and money.

The emergency medical technician will typically follow the below listed steps to deploy the splint 21, 115, or 121. First, the splint 21, 115 or 121 will be removed from and package in which it is shipped, typically by peeling open a mylar pouch. The package will be discarded. The splint 21, 115 will be opened so that the two members 23, 25 are separated. The first and second enclosures 35 and 45 are opened, whether by tearing a strip 103, or by separating upper and lower sealing ribs 95 and 97. Water, if available, is then added to begin the curing process on both the first and second sheets of formable material 81 and 93. The formable material 81 and 93 will harden without water; however, the time to harden without water will increase significantly.

The first and second flag of hook members 37 and 87 are then closed to envelope the first and second sheets of formable material 81 and 93. Next, place the three flexible members 27 under the limb so that the first and second members 23 and 25 are cradling the limb. Position each of the first and second members 23 and 25 around the limb so that the limb is cradled by each member 23 and 25.

If the limb is smaller than the selected splint 21 or 115, make sure that the member 23 and 25 and not the flexible members 27 are cradled against the limb. Take each of the four flexible hook fasteners 43 and wrap the strips around the circumference of the limb, spacing equally along the length of the splint 21. Please make sure that the four flexible hook fasteners 43 are snug, but not too tight. Over tightening the four flexible hook fasteners 43 will restrict the bladders 31 and 67. Mold the members 23 and 25 along the limb and ensure proper position. The first and second sheets of formable material 83 and 93 will take approximately three to six minutes to harden when moistened. Proper positioning at this time will ensure optimal performance of the splint 21 and 115. The splint 121 will be attached in the same fashion, but only one opening and application of water to the formable material 135 need be made.

Next the squeeze bulb 51 is grasped and its associated fitting 57 attached to one of the fittings 59 and 61. Each of the bladders 31 and 67 are then inflated until they are filled partially with air. Each port should be insured to be in a closed position prior to detaching the inflation squeeze bulb 51. Care should be taken so as to not over-inflate as this will tend to straighten out the sheets of formable material 81 and 93.

Re-adjust the tightness of the flexible hook fasteners 43 to ensure a snug, but comfortable fit. Check the position and hardness of the formable material 81 and 93. Once they are rigid, final adjustments on the inflation bladders 31 and 67 and flexible hook fasteners 43 position can be determined. The patient should now otherwise be ready for transport.

While the present invention has been described in terms of a splint or cast medical device, one skilled in the art will realize that the structure and techniques of the present invention can be applied to many appliances. The present invention may be applied in any situation where rapid deployment of a more permanent limb or extremity support and protection is sought.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed is:

1. A splint for immobilizing an extremity, comprising a first rectangular support including a first pressurizable bladder and a first area of formable material which is formable to a first shape of the extremity and hardenable to maintain said first shape, said first support having a first edge and a second edge opposite said first edge, said first and second edges along a longer dimension of said first rectangular support;

a second rectangular support including a second pressurizable bladder and second area of formable material which is formable to a second shape of the extremity and hardenable to maintain said second shape, said second support having a first edge and a second edge opposite said first edge, said first and second edges along a longer dimension of said second rectangular support;

each of said first and second rectangular supports having a first exterior layer with a first exterior surface adapted to be disposed away from the extremity and a second exterior surface adapted to be disposed toward the extremity, said first and second pressurizable bladders each having a first exterior side material forming said second exterior surface of each rectangular support and an adjacent second exterior side material;

said first area of formable material encased and surrounded by a first water impermeable enclosure stitchably attached between said first exterior layer and said second exterior side material of the first pressurizable bladder of said first rectangular support, and said second area of formable material encased and surrounded by a second water impermeable enclosure stitchably attached between said first exterior layer and said second exterior side material of the second pressurizable bladder of said second rectangular support, said first and said second water impermeable enclosures openable to expose said first and said second areas of formable material, respectively;

a plurality of spaced apart connection straps having first ends connected to said first rectangular support adjacent said first edge of said first rectangular support and second ends connected to said second rectangular support adjacent said first edge of said second rectangular support;

a plurality of spaced apart fastening straps having first ends connected to said first rectangular support adjacent said second edge of said first rectangular support and second ends connected to said second rectangular support adjacent said second edge of said second rectangular support; and a bladder inflation device connectable to said first and said second bladders.

2. The splint for immobilizing an extremity as recited in claim 1, wherein said first and second enclosures are re-closable to a sealed condition.

3. The splint for immobilizing an extremity as recited in claim 2, wherein said first and second areas of formable material include fiberglass cloth.

4. A splint for immobilizing an extremity, comprising:

a pressurizable bladder having a first layer of material having a first side for directly opposing and contacting the extremity to be immobilized and a second side, a second layer of material having a first side and a second side opposing said second side of said first layer of material, said first and said second layers of material sealably joined adjacent their respective edges to form said pressurizable bladder;

a third layer of material adjacent said first side of said second layer of material, said third layer of material curable to a rigid shape conforming to the shape of the extremity to be immobilized;

a fourth layer of material securing said third layer of material adjacent at least one of said first and said second layers of material, and stitchably joined to one of said first and said second layers of material;

said third layer of material encased in a water impermeable enveloping material, said water impermeable enveloping material adjacent said first side of said second layer of material and said fourth layer of material, said water impermeable enveloping material having an edge portion stitchably joined to and between one of said first and second layers of material and said fourth layer of material;

securing members attached to said fourth layer of material to secure said splint around the extremity; and a pressure inflation device having a fluid output in fluid communication with said pressurizable bladder between said first and said second layers of material, wherein said securing members secure said splint around the immobilized member and engage and fasten to said fourth layer of material.

5. The splint for immobilizing an extremity as recited in claim 4, wherein said water impermeable enveloping material is selectively openable to access said third layer of material and sealable to isolate said third layer of material.

6. The splint for immobilizing an extremity as recited in claim 4, wherein said third layer of material further comprises fiberglass cloth.

* * * * *